US00PP35752P2

(12) United States Plant Patent
Davis

(10) Patent No.: US PP35,752 P2
(45) Date of Patent: Apr. 16, 2024

(54) HOLLY TREE NAMED 'CDAV247'

(50) Latin Name: *Osmanthus heterophyllu*
Varietal Denomination: CDAV247

(71) Applicant: Chris W. Davis, Virginia Beach, VA (US)

(72) Inventor: Chris W. Davis, Virginia Beach, VA (US)

(73) Assignee: Chris W. Davis, Virginia Beach, VA (US)

( * ) Notice: Subject to any disclaimer, the term of this patent is extended or adjusted under 35 U.S.C. 154(b) by 0 days.

(21) Appl. No.: 18/169,385

(22) Filed: Feb. 15, 2023

(51) Int. Cl.
*A01H 6/00* (2018.01)
*A01H 5/00* (2018.01)

(52) U.S. Cl.
USPC ..... Plt./247

(58) Field of Classification Search
USPC ..... Plt./247
CPC ..... A01H 6/00; A01H 5/00; A01H 5/12
See application file for complete search history.

*Primary Examiner* — Keith O. Robinson
(74) *Attorney, Agent, or Firm* — The Webb Law Firm

(57) ABSTRACT

A new and distinct variety of holly tree with large blooms, suitable for foundation, hedge, or specimen planting.

12 Drawing Sheets

Botanical classification: *Osmanthus heterophyllu.*
Varietal denomination: 'CDAV247'.

BACKGROUND OF THE INVENTION

The present invention comprises a new and distinct *Osmanthus heterophyllu* tree known by the varietal name 'CDAV247'. The new variety was discovered as a unique mutation of variegated holly in a cultivated state in 1990. The first act of asexual reproduction was in May of 2021, by cuttings, in Virginia Beach, Virginia. Observations of the new variety have shown that the unique features of 'CDAV247' are stable and have reproduced true to type in successive generations. The variety 'CDAV247' has not been evaluated under all possible environmental conditions. The phenotype may vary with variations in environment without a change in genotype.

When compared to other holly varieties known to the applicant, such as the variety 'Heckenstar' as disclosed in U.S. Plant Pat. No. 14,308, 'CDAV247' can be distinguished based on its winter flowering, the size and concentration of its blooms, which are larger than typical hollies, its tri-color foliage, the fragrance of its blooms, its regular production of near albino leaves, the lack of recessive to solid green foliage, the presence of 4-5 thorny spikes on leaf sides and tips on leaves on the lower half of the tree, and its strong rootstock, which does not require grafting.

DESCRIPTION OF THE DRAWINGS

The accompanying photographic drawings illustrate the new variety at close to 32 years of age, with the color being as nearly true as is possible with color illustrations of this type.

DESCRIPTION OF THE PLANT

Figure 1:
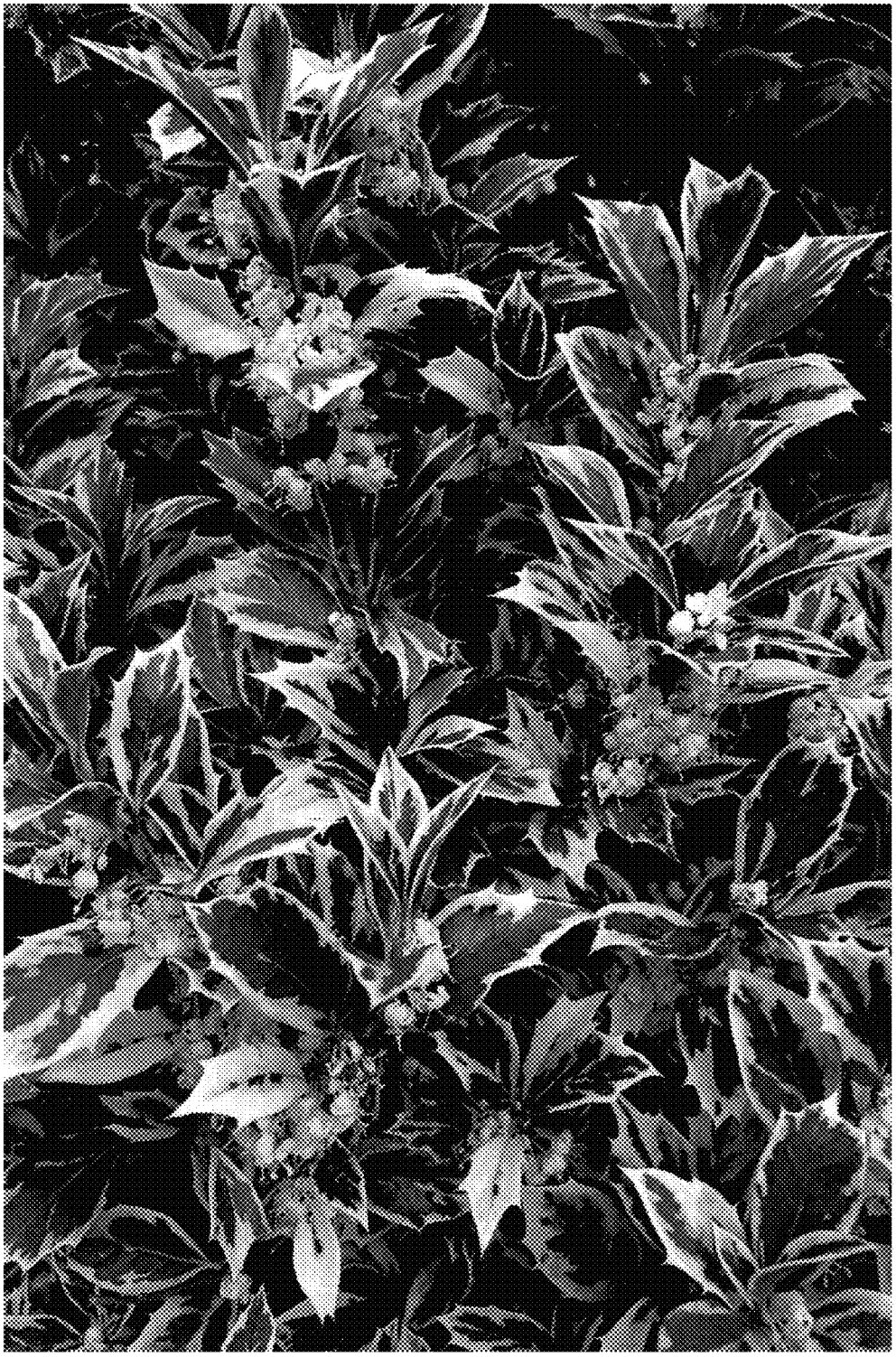
FIG. 1 shows a close up view of foliage and blooms of the new variety.
Figure 2:
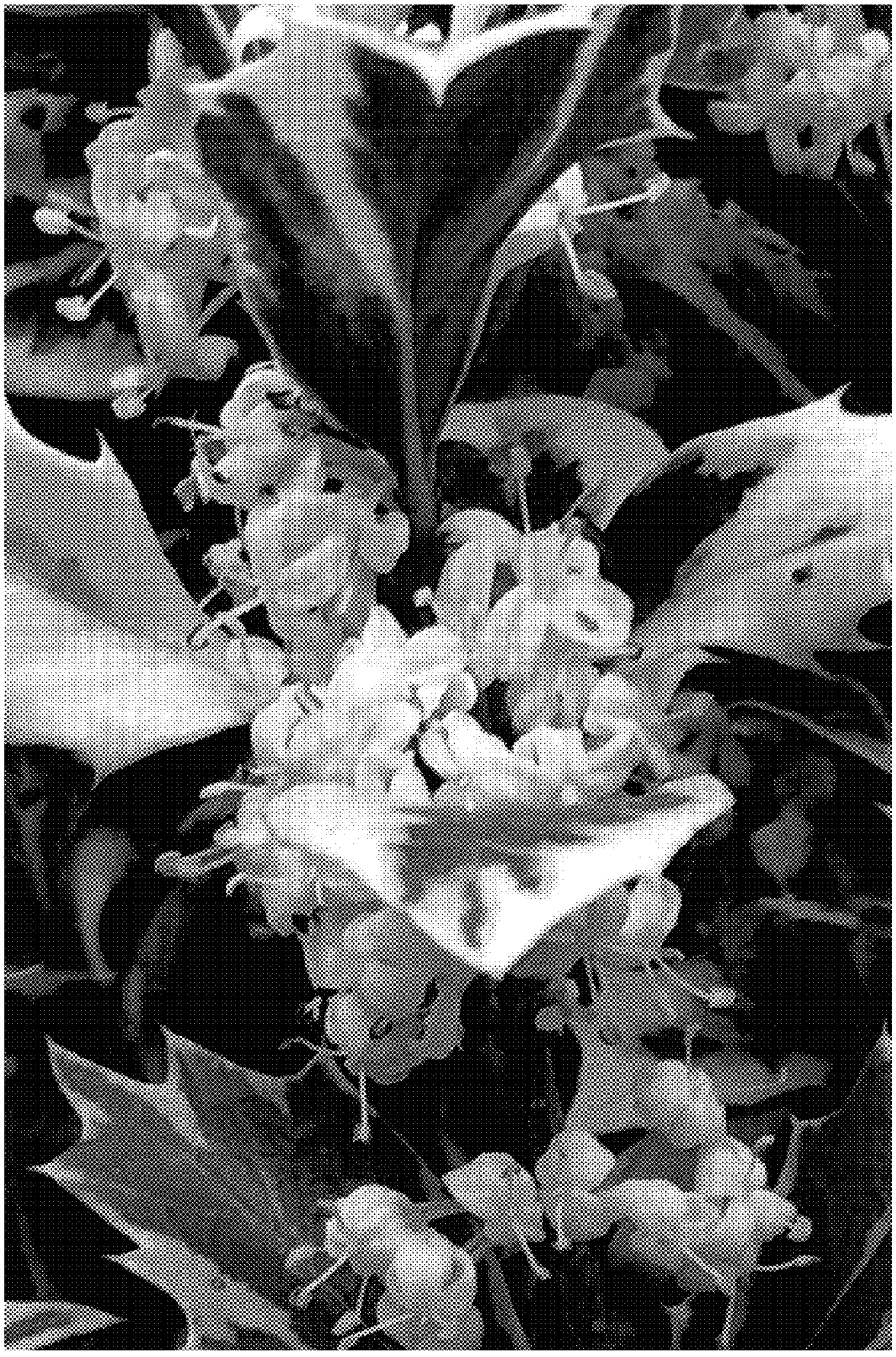
FIG. 2 shows a close up view of blooms of the new variety.
Figure 3:
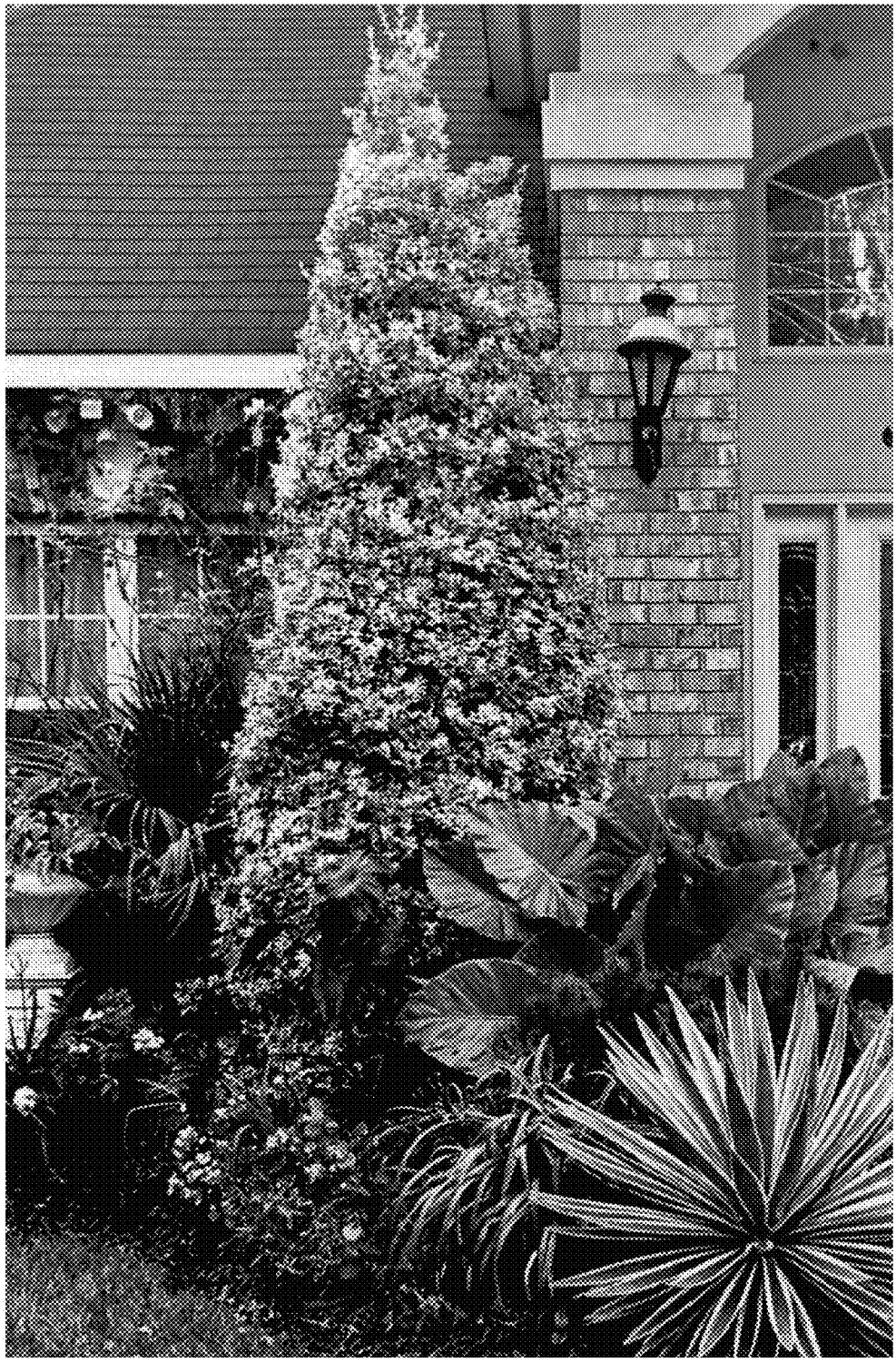
FIG. 3 shows a full view of the new variety, showing overall plant habit.
Figure 4:
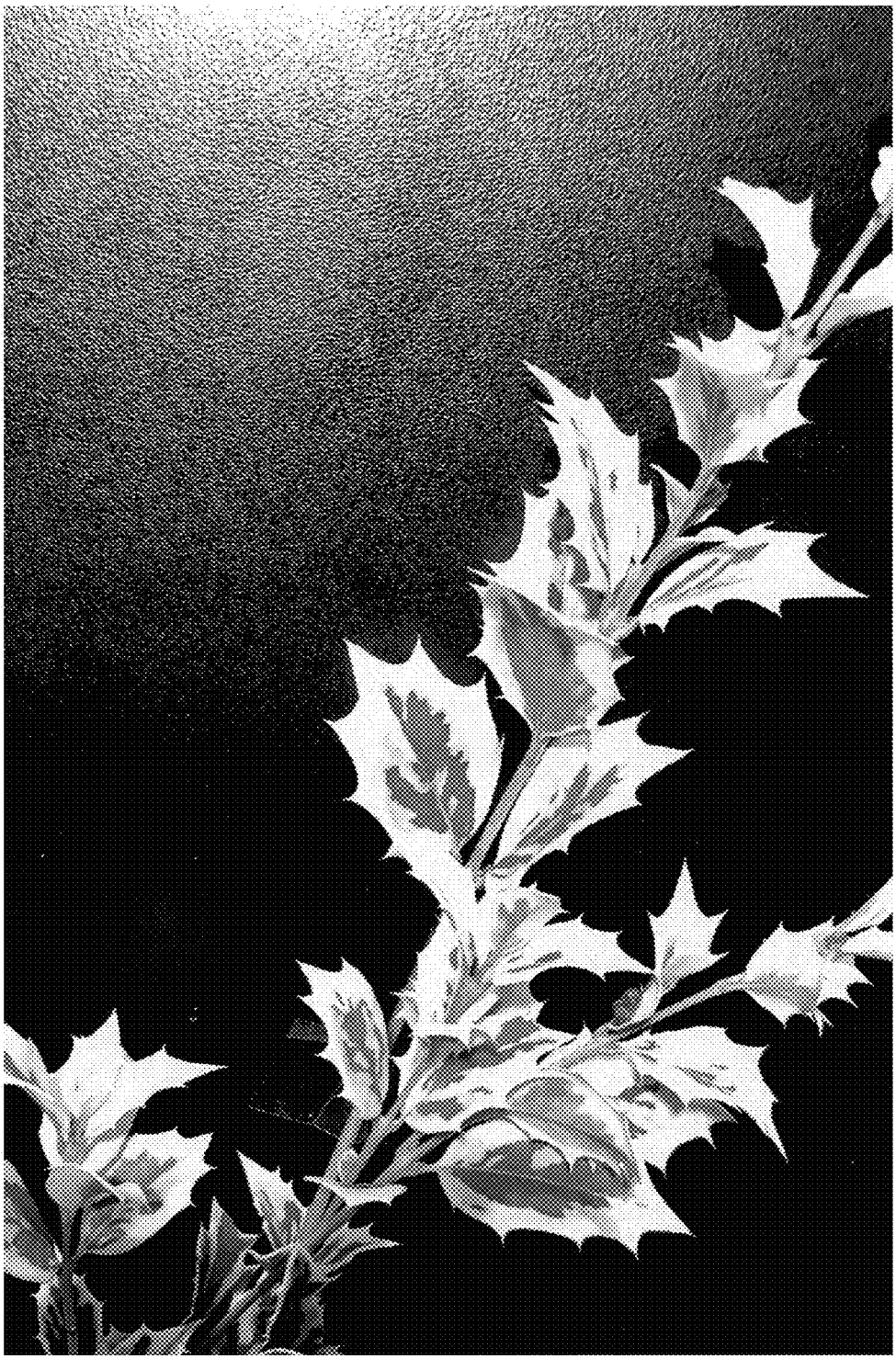
FIG. 4 shows a close up of foliage of the new variety.
Figure 5:
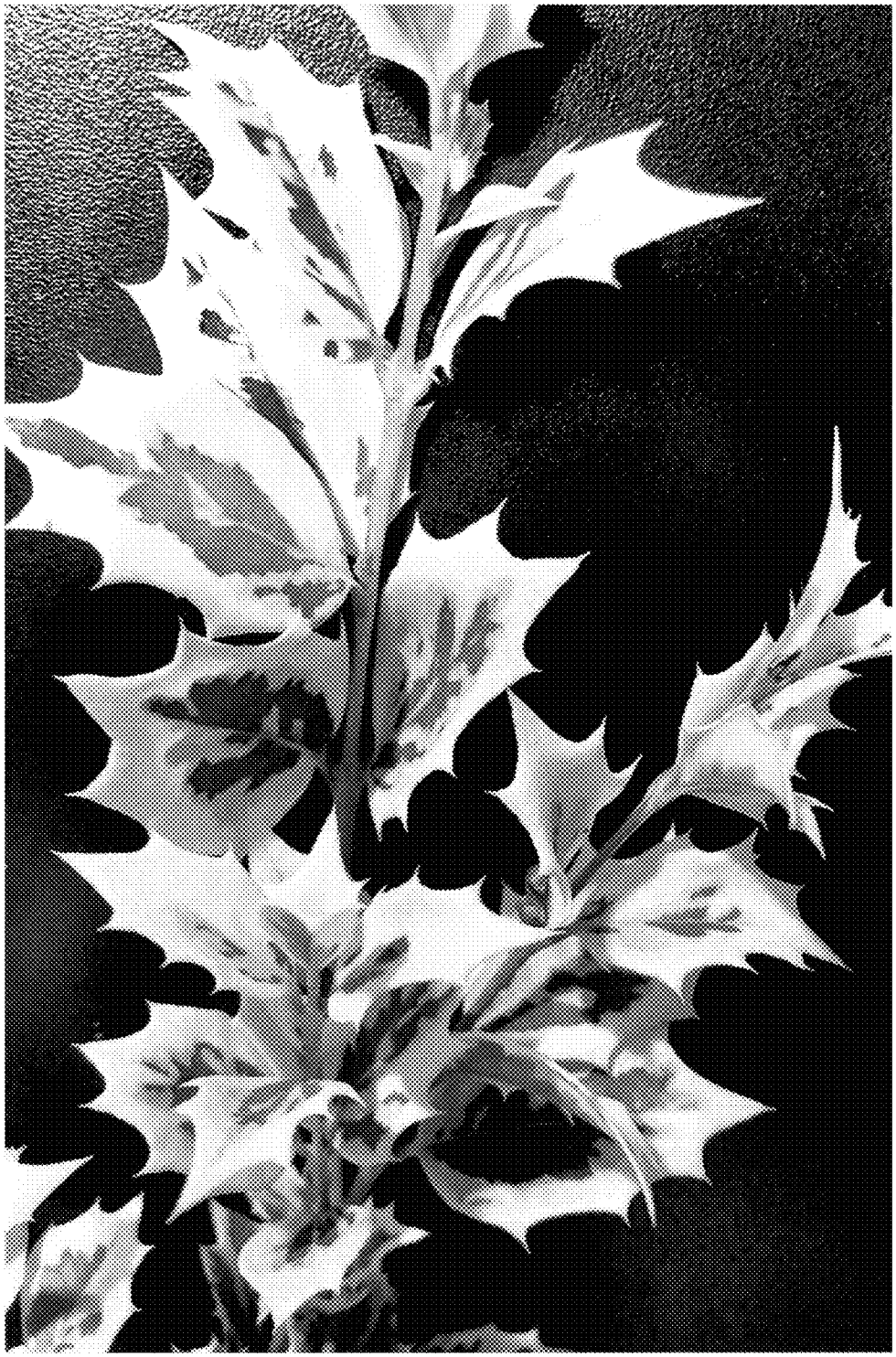
FIG. 5 shows a close up of foliage of the new variety
Figure 6:
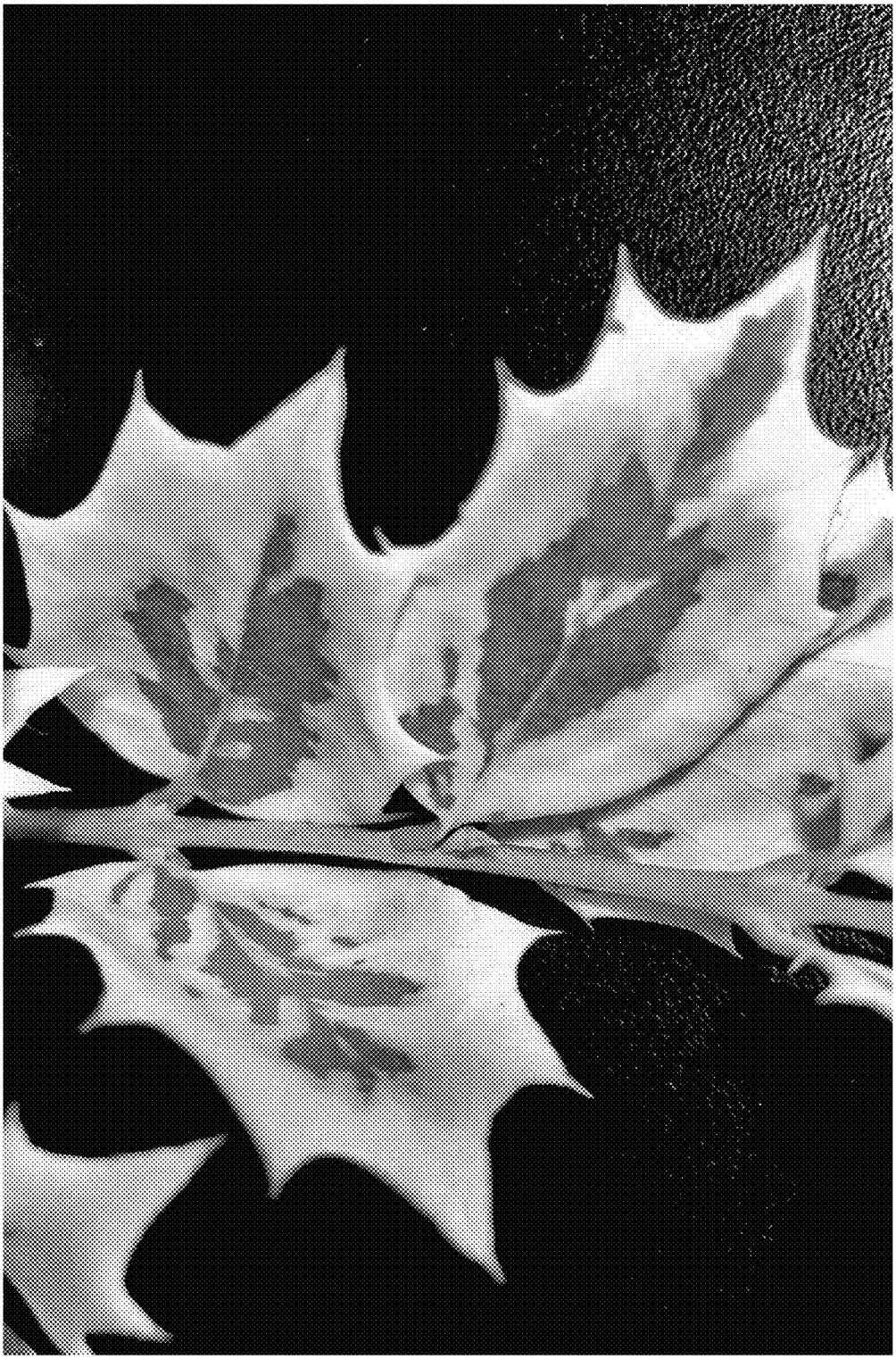
FIG. 6 shows a close up of foliage of the new variety.
Figure 7:
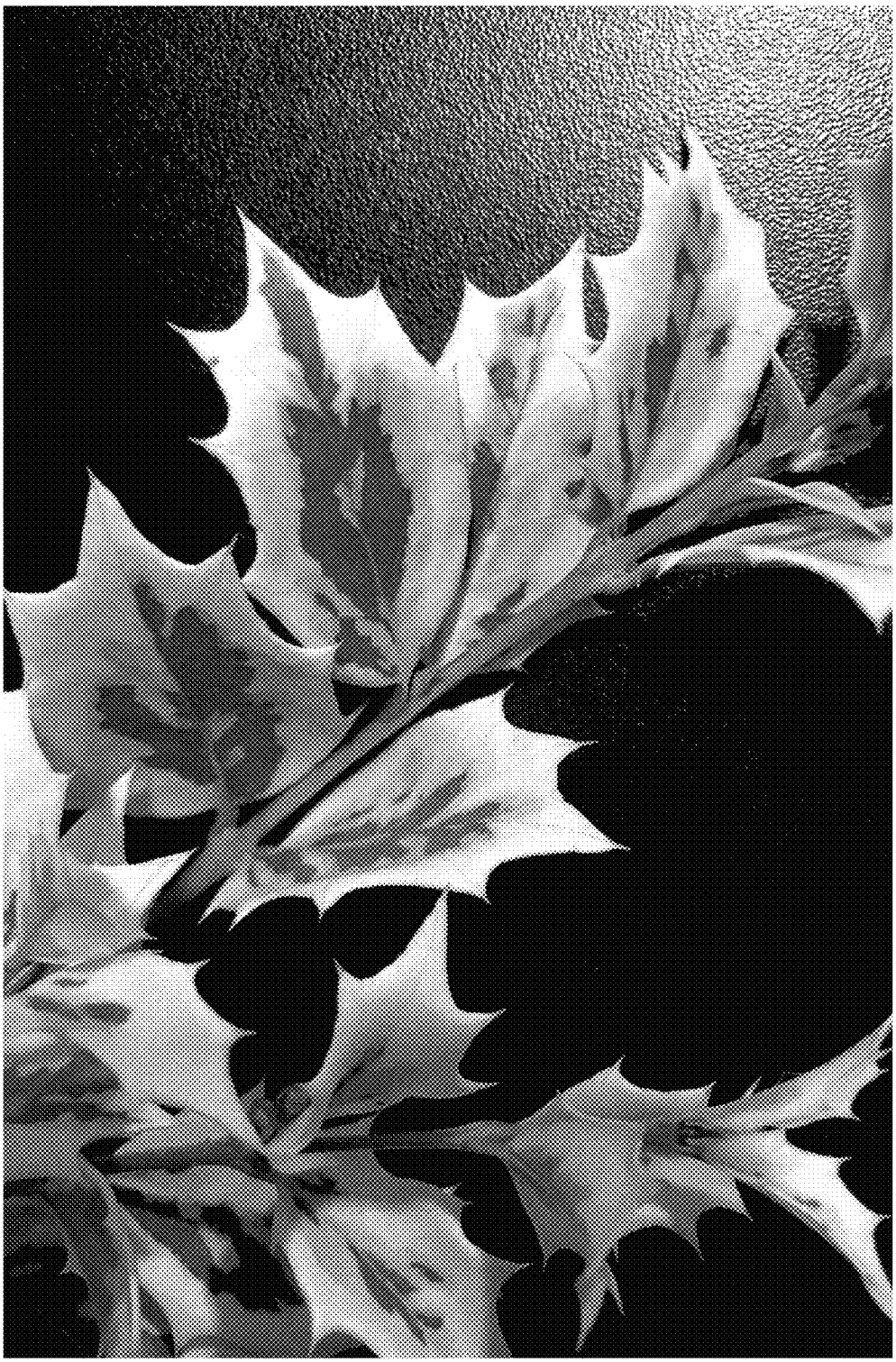
FIG. 7 shows a close up of foliage of the new variety.
Figure 8:
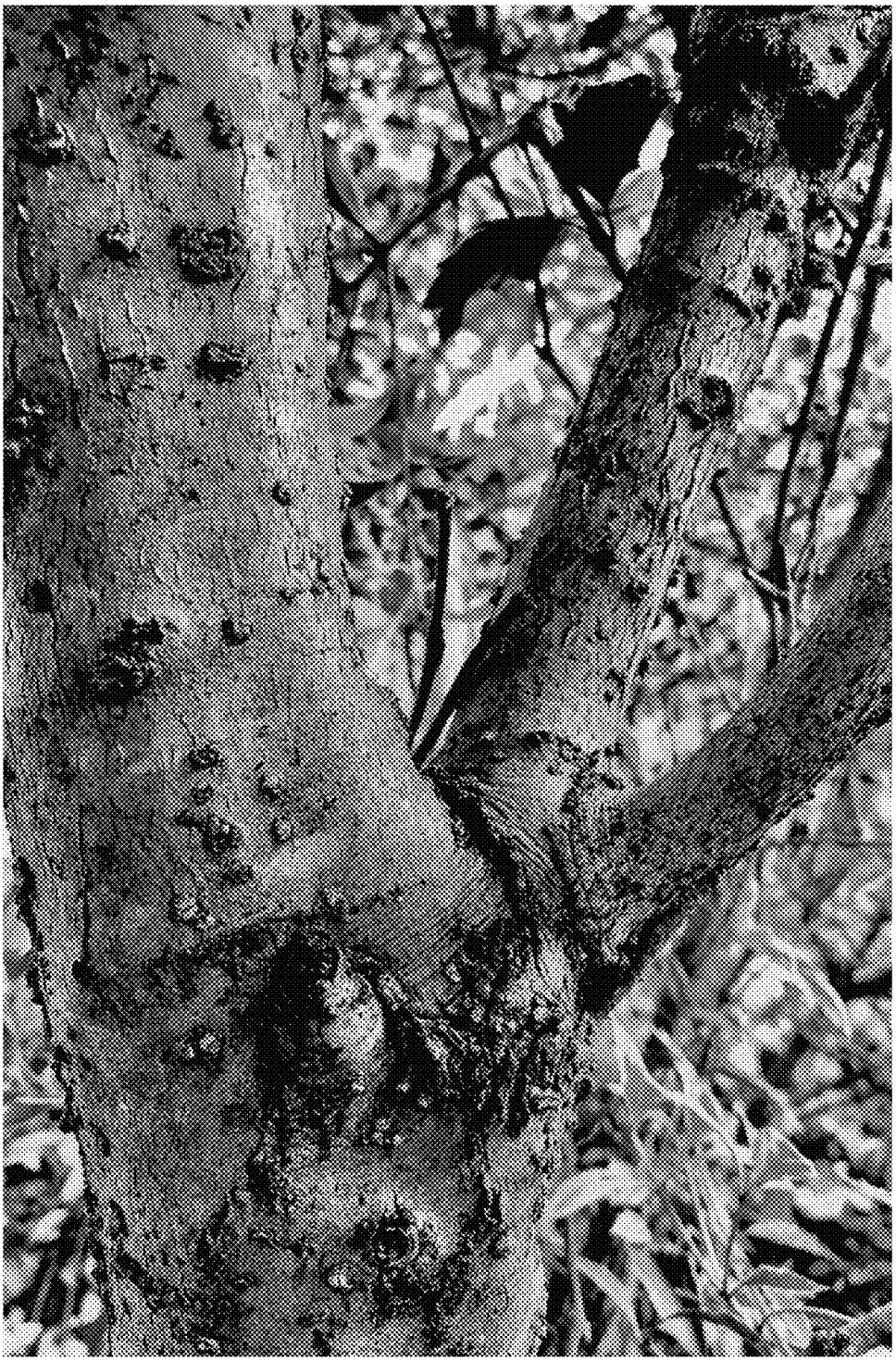
FIG. 8 shows the trunk and branches, including lenticels, of the new variety.
Figure 9:
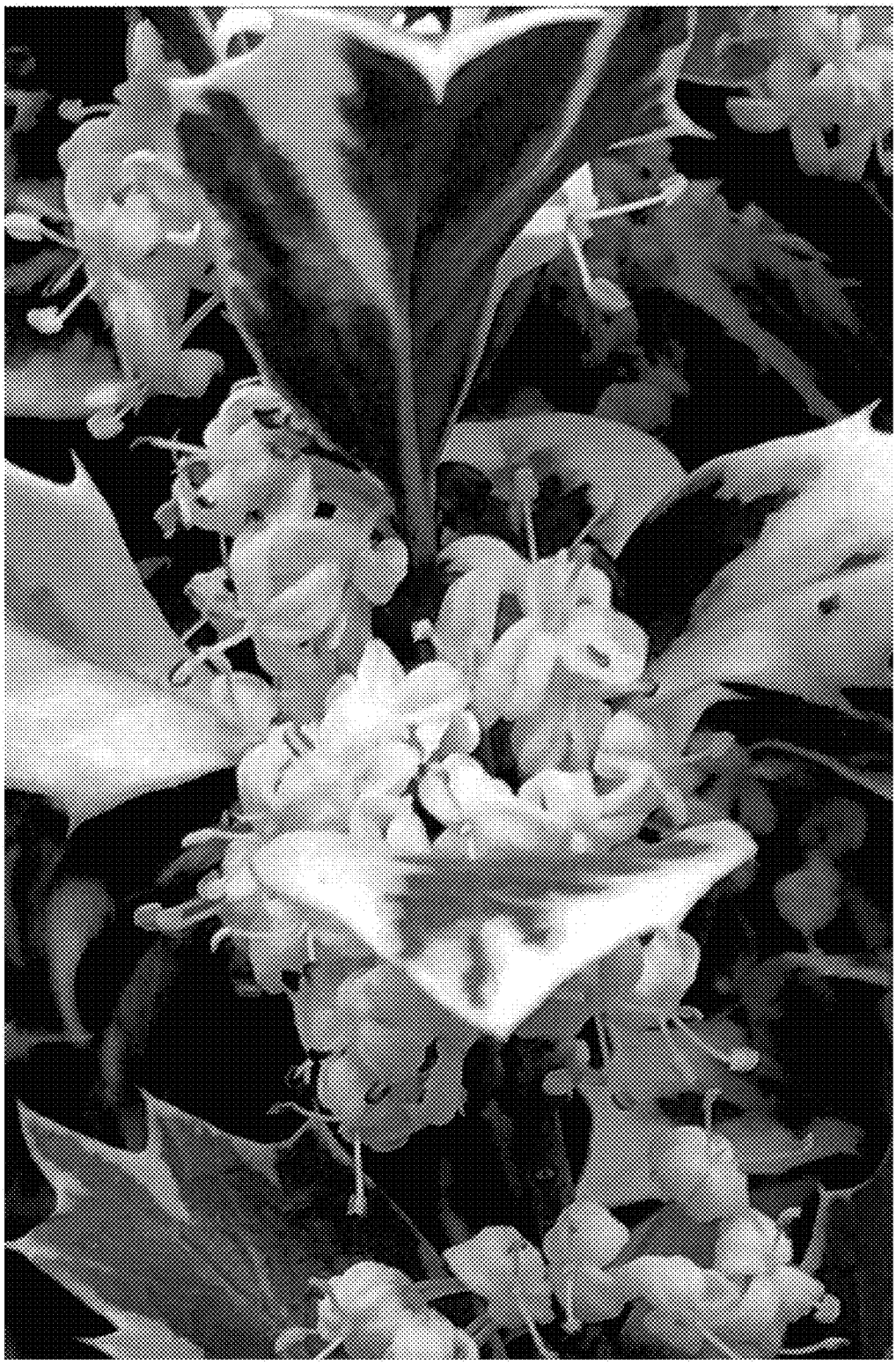
FIG. 9 shows bloom shape and color of the new variety.
Figure 10:
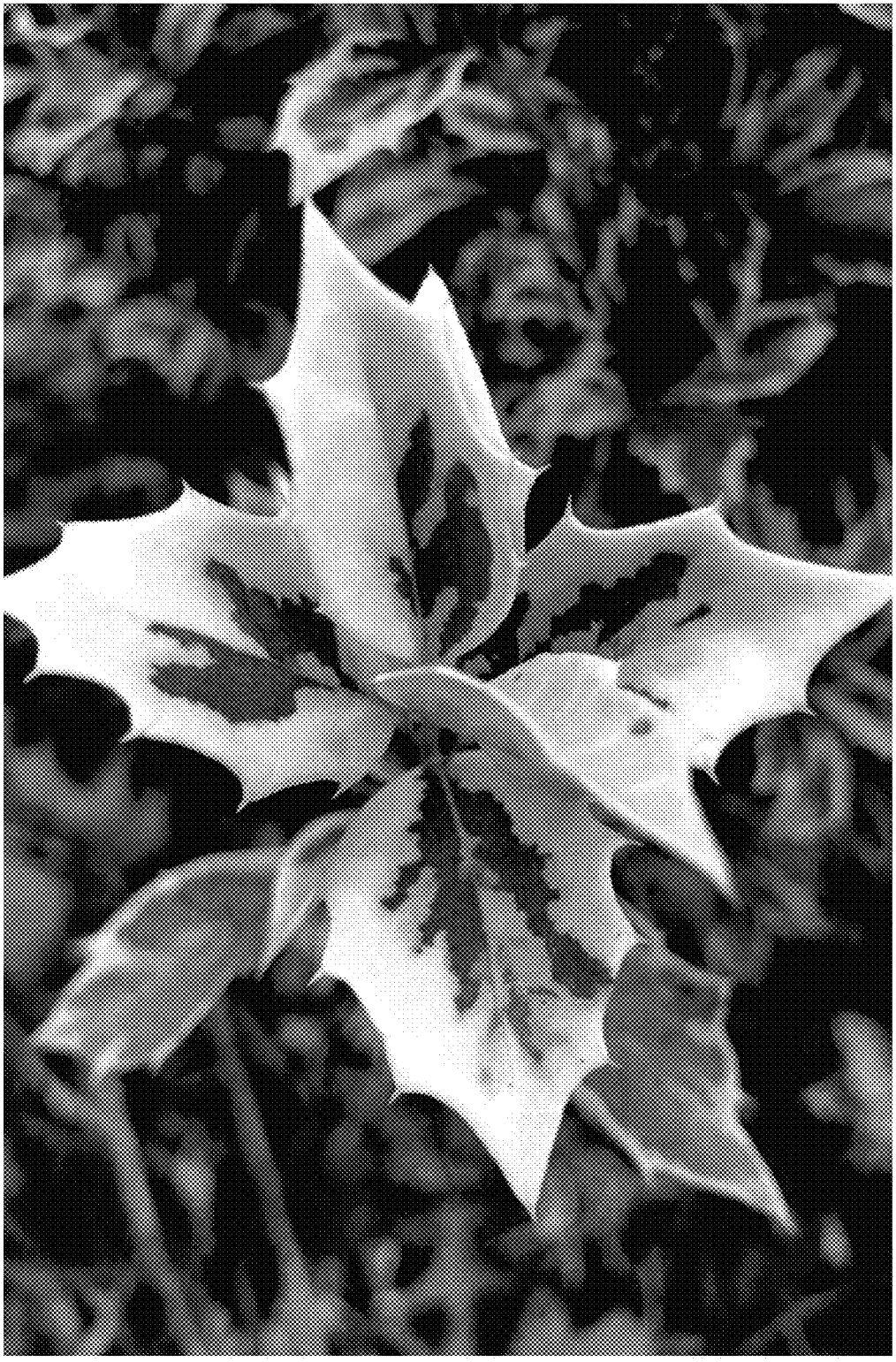
FIG. 10 shows the alternating leaf pattern of the new variety.
Figure 11:
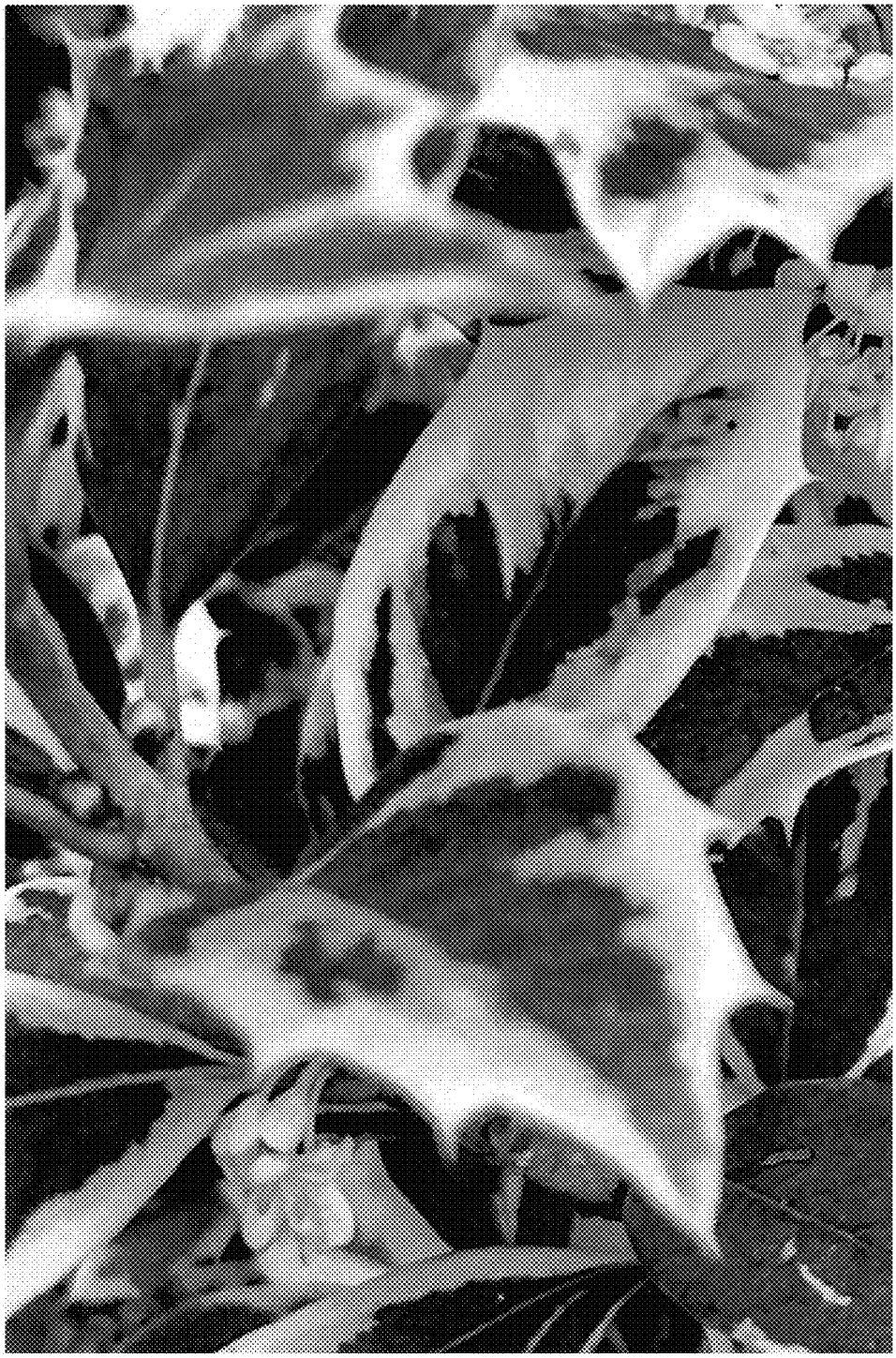
FIG. 11 shows a close-up of a branch and buds, including mature lenticels and bark, of the new variety.
Figure 12:
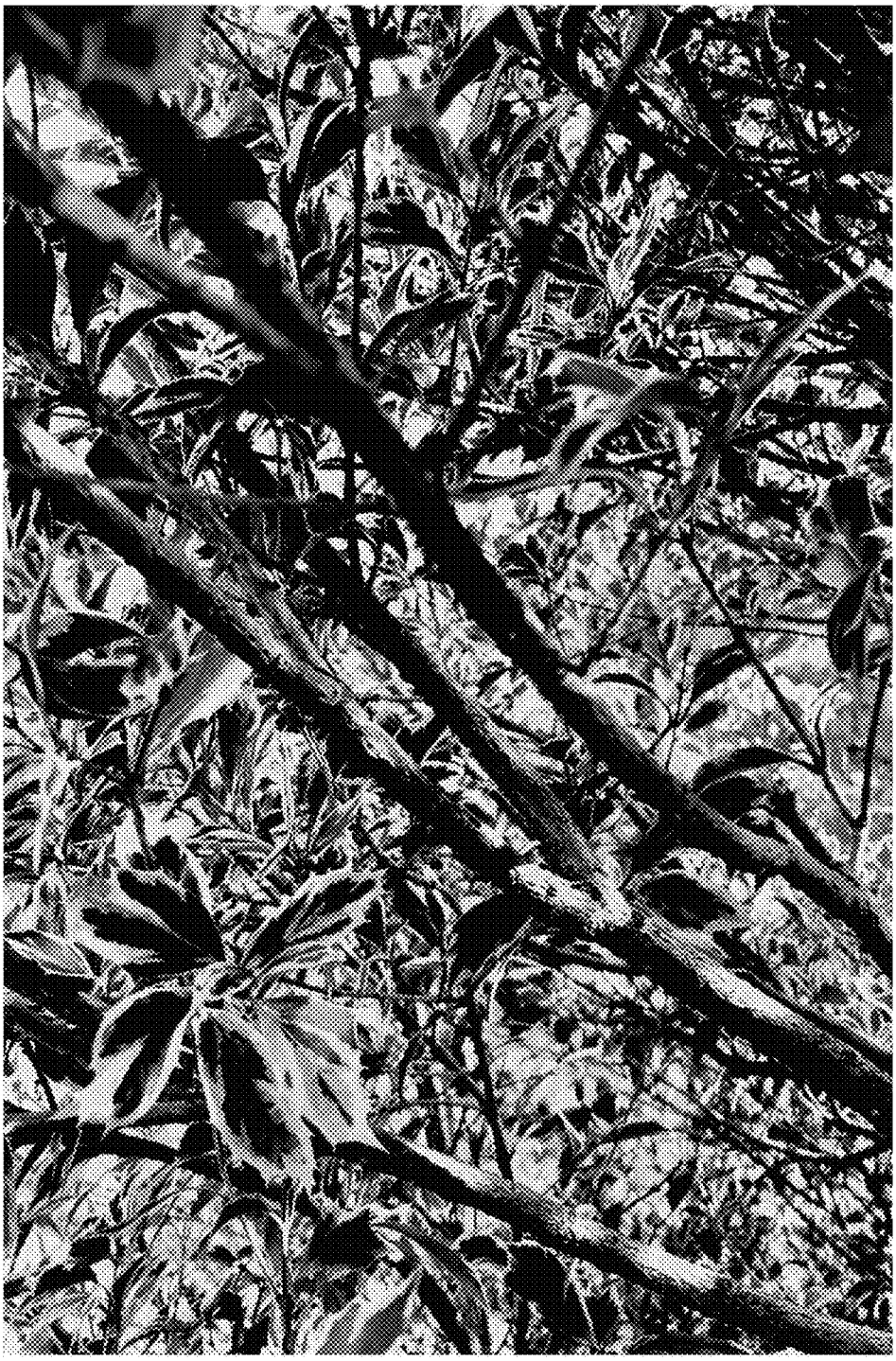
FIG. 12 shows branches, including maturing lenticels and bark, of the new variety.

The following detailed description sets forth the characteristics of the new variety. The new variety has been grown in moist, yet well-drained soil. The soil is rich in natural compost, with added sand and peat moss (average pH of 6-7). 'CDAV247' was grown in Virginia Beach under natural light. Growth conditions for 'CDAV247' include a USDA Plant Hardiness Zone of 8-8.5 (four seasons, moderate Southern U.S. temperatures), a coastal location (about 8 miles from the Atlantic Ocean), sunny exposure with rare snow, and soil with humic acid. Blooming occurs in the fall in North America, typically in November. The variety 'CDAV247' tolerates moist loamy soil, sandy soil, peaty soil, acidic soil, and calcareous soil, prefers USDA Plant Hardiness Zones of 5-9, and has tolerated temperatures as low as 15 degrees Fahrenheit. The color readings and measurements listed hereinafter were taken in Virginia Beach in November, 2022, under natural light on 18-month-old rooted cuttings. Color references are primarily to the 2015 R.H.S. Colour Chart of The Royal Horticultural Society of London. 'CDAV247' has been asexually reproduced by cuttings (8" cuttings in soil) since May, 2021.

'CDAV247' is sterile (contains no seeds or berries), which allows for the new variety to be non-invasive.

PLANT

The following is a detailed description of 'CDAV247'. Data was collected in Virginia Beach, Virginia from 18-month-old rooted cuttings grown outdoors in one-gallon plastic pots. Height measurements were taken from soil level to 9 inches of the plastic pot containers. Throughout this specification, color names beginning with a small letter signify the name of that color, as used in common speech, where aptly descriptive. Color names beginning with a capital letter designate values based upon the 2015 R.H.S. Colour Chart of The Royal Horticultural Society of London.

'CDAV247' is a medium-sized tree with a densely defined pyramidal crown that matures to a height of about 15 feet and a width of about 6 feet at the base (the trunk base is normally below 7 inches wide and tapers). The leaves are narrow-ovate to elliptical. 'CDAV247' regularly produces near albino leaves. Leaves on the lower half of the tree include sharp, protective spikes (4-5 spikes) on each side of the leaf and on the tip. The upper half of 'CDAV247' is less armed. 'CDAV247' blooms in November in Virginia Beach, Virginia, with large flowers that smell intensely of rose or of daphne. 'CDAV247' has been observed to be sterile, and thus does not produce fruit. 'CDAV247' prefers USDA Plant Hardiness Zones of 5-9, with sunny exposure, use of humic acid, and moist, well-drained soil. 'CDAV247' tolerates acidic or calcareous soil, tolerates wind very well, and is suitable for foundation, hedge, or specimen planting. Grafting is not necessary as 'CDAV247' exhibits a strong natural root system.

Habit: Upwards. Overall plant shape is upright; narrowly pyramidal.

Vigor: Growth rate of 6 inches to 12 inches per year on average, with year-round growth; fairly vigorous.

Rooting habit: not readily available.

Size of plant:

- *A. Height.*—15 feet on an approximately 27-year-old tree, with approximately a 6-foot spread at maturity.
- *B. Width.*—Trunk: 4-7 inches, overall; 6 feet at the widest point (several feet from ground level).

Stem:

- *A. Color.*—RHS 161B maturing to RHS 199D.
- *B. Texture.*—New stems are under ⅛ of an inch wide, are flexible and smooth to the touch, maturing to flexible woody texture, ¾ of an inch wide, under 1-inch branches.
- *C. Appearance/shape.*—Rounded with smooth bark.
- *D. Aspect/angle.*—Main trunk is around 90 degrees (perpendicular with the ground); lateral branches are 20-45 degrees.

Immature lenticels:

- *A. Shape.*—Varied, circular, elliptical, elongated.
- *B. Position relative to stem surface.*—Visible on all mature wood that are one year old or older.
- *C. Average length.*—Under ½ of an inch on average.
- *D. Average width.*—Varies from round to horizontal-oval.
- *E. Quantity.*—Varies in irregular patterns.

Mature lenticels:

- *A. Shape.*—Irregular in shape and size, concentrated at branch points, size is not readily available.
- *B. Average length.*—Trunk is 15 feet tall on an approximately 27-year-old tree; secondary branches are under 36 inches in length; lateral branches around 90 cm in length, mature lenticels average about 0.5 to about 0.75 of an inch in length.
- *C. Average width.*—Trunk base is approximately 4.5 inches in diameter; secondary branches are under 3 inches wide; lateral branches about 2 mm in diameter when young, growing to about 8 mm when mature; mature branches are about 2.5 to about 7.5 cm in diameter; internode length of about 7 cm, lenticels average about 0.12 of an inch in width.

Leaf:

- *A. Type.*—Narrow-ovate to elliptical, tip is acuminate/spinose and base is cuneate, variegated leaves.
- *B. Mature size* (*l*×*w*).—6 centimeters×3 centimeters (average).
- *C. Margins.*—Lobed, 3-4 pairs of spine-bearing triangular lobes.
- *D. Spine quantity and location.*—Up to 4 spines on both leaf sides to leaf point/spin.
- *E. Upper surface.*—Glabrous with minor raised venation present, glossy, and unremarkable venation color; RHS NN137C with RHS 8D marginal variegation.
- *F. Lower surface.*—Glabrous with minor raised venation present; RHS 147C to RHS 148C with RHS 8D marginal variegation.
- *G. Petiole.*—About 5 mm in length and about 2 mm in diameter, glabrous and RHS N144D on upper and lower surfaces.
- *H. Leaf arrangement.*—Opposite decussate.
- *I. Venation pattern.*—Pinnate, RHS N144D on upper and lower surfaces.

Flower:

- *A. Size.*—About 5 mm in height and about 7.5 mm in width.
- *B. Peduncle.*—Glabrous, RHS 157A, about 4 mm in length, about 1 mm in diameter, about a 20-45 degree angle relative to the stem; good strength, with some flexibility.
- *C. Calyx and sepals.*—Absent.
- *D. Fragrance.*—Fragrant, daphne- or rose-scented.
- *E. Bud.*—RHS 157A and tear-drop shaped, with unremarkable color change during opening; hundreds of buds per lateral stem, length of about 3 mm and diameter of about 2 mm.
- *F. Blooms.*—Tubular with a four-lobed corolla; color (R.H.S.): White 155B; longevity: 2-3 weeks; petals are glabrous on upper and lower surfaces and slightly fleshy, pure-white and shiny, four elliptical, fused petals, obtuse at the tip and fused at the base, having an entire margin, petal size is about 5 mm in length and about 2.5 mm in width; petal color is RHS NN155B-c on upper and lower surfaces when opening and fully opened.
- *G. Arrangement.*—In cymes along the length of lateral branches, hundreds of flowers per lateral stem, 4-5 flowers per inflorescence on average.
- *H. Flowering season.*—Autumn (October-November).
- *I. Aspect.*—Outward.
- *J. Shape.*—Campanulate with a four-lobed corolla; petal arrangement is cruciform and the petals are reflexed/curled toward the pedicel.

*K. Size.*—About 5 mm in length, about 2 mm in height, and about 5 mm in diameter.

*L. Persistence.*—Self-cleaning.

Reproductive organs:

*A. Stamens.*—2, less than 1 mm in length, RHS 155B; white and oval-shaped anthers under ⅛ of an inch in length; produces a moderate amount of RHS 160D pollen.

*B. Pistils.*—None.

*C. Anther.*—Ovoid shape, about 1 mm in length, RHS 160B.

Resistance: Highly disease- and pest-resistant; resistant to damage from spider mites (*Tetranychus urticae*) and to infection from *Oomycete* organisms and *Phytophthora ilicis.*

Hardiness: Excellent winter hardiness; the trees have been grown in USDA zone 8a, and have survived 15 degrees Fahrenheit with no damage (in Virginia Beach, Virginia).

Drought/heat tolerance: Excellent.

The invention claimed is:

1. A new and distinct variety of *Osmanthus heterophyllu* holly tree named 'CDAV247', as is herein illustrated and described.

* * * * *